United States Patent [19]

Moulton

[11] Patent Number: 5,408,184
[45] Date of Patent: Apr. 18, 1995

[54] CONSTANT-TEMPERATURE JACKET FOR SYRINGE-TYPE ELECTROLYTE CONDUCTIVITY TEST CELLS

[75] Inventor: Russell D. Moulton, San Jose, Calif.
[73] Assignee: Valence Technology, Inc., San Jose, Calif.
[21] Appl. No.: 42,304
[22] Filed: Apr. 2, 1993
[51] Int. Cl.⁶ ........................................... G01N 27/28
[52] U.S. Cl. ................................ 324/450; 324/439; 204/408
[58] Field of Search ................ 324/439, 450; 204/408, 204/409

[56] References Cited

U.S. PATENT DOCUMENTS 3,997,420 12/1976 Buzza .............................. 324/450 X
4,835,477 5/1989 Palaschegg et al. ................. 324/439
5,025,219 6/1991 Gaspard .......................... 324/439 X
5,220,283 6/1993 Dentel ............................... 324/453

Primary Examiner—Kenneth A. Wieder
Assistant Examiner—Glenn W. Brown
Attorney, Agent, or Firm—William Johnson

[57] ABSTRACT

An apparatus for measuring the conductivity of an electrolyte comprises at least one conductivity cell, e.g., syringe-type conductivity cell and a constant temperature jacket. The syringe-type conductivity cell preferably employed in the apparatus comprises a generally longitudinal, cylindrical wall and two electrode rods which serve to define a volume for testing the conductivity of a sample in the volume. The constant temperature jacket comprises at least one longitudinal chamber for holding a conductivity cell, a temperature sensing device, and a fluid channel which is in fluid communication with a source of constant temperature fluid.

6 Claims, 1 Drawing Sheet

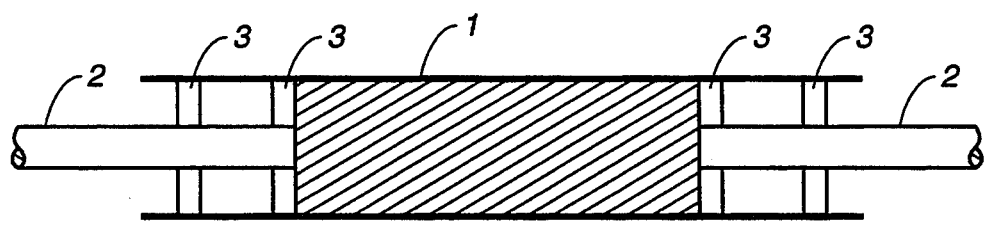
FIG._1
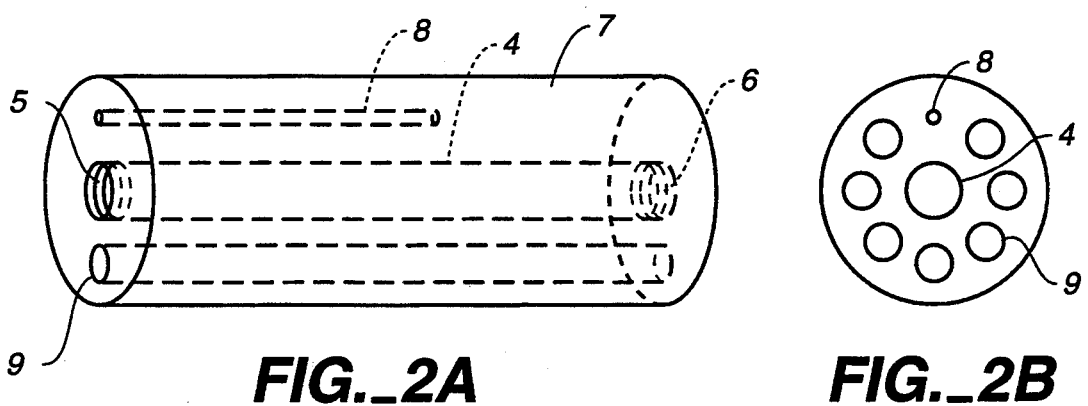
FIG._2A  FIG._2B

CONSTANT-TEMPERATURE JACKET FOR SYRINGE-TYPE ELECTROLYTE CONDUCTIVITY TEST CELLS

FIELD OF THE INVENTION

The present invention relates to an apparatus for measuring the conductivity of an electrolyte which includes a syringe-type conductivity cell and a constant temperature jacket. In particular, this apparatus will allow measurements to be made at a variety of reproducible temperatures from, e.g., as low as −30° C. to as high as +85° C. or above.

BACKGROUND OF THE INVENTION

In the past, the art has employed differing techniques for determining the conductivity of solid electrolyte. For example, an alternating electrical current has been introduced across two electrodes between which a film of the electrolyte is located. Such an arrangement can be sealed within a container containing an inert atmosphere so as to protect the film from moisture. Moreover, due to the temperature dependence of ionic conductivity, this container has been placed in a constant-temperature chamber. However, such arrangements have been considered bulky and cumbersome.

Recently, an improved conductivity cell has been produced. This cell, which was developed by Ib Olsen of Valence Technology, Inc., Denmark, is known as syringe-type electrolyte conductivity cell and is illustrated in FIG. 1 (as disclosed in U.S. patent application Ser. No. 08/042,315 which is filed as Attorney Docket No. 1154 and entitled "ELECTRO CHEMICAL TEST CELL FOR TRANSPORT AND CONDUCTIVITY MEASUREMENTS" which application is incorporated herein by reference in its entirety).

In FIG. 1, such a conductivity cell comprises a plastic barrel, 1, adapted from a syringe by cutting off the tip of the barrel, and pair of metal, electrode-rods 2, each having at least one O-ring, 3, located thereon.

In such a cell, a sample of unpolymerized electrolyte can be placed into the syringe barrel and sealed between the two metal rods or electrodes. This sample can then be cured "in-situ" by employing ultraviolet radiation, or heat. Alternatively, a sample of thermoplastic material can be drawn into the cell (syringe barrel) at elevated temperatures where the thermoplastic is fluid. The sample may then be allowed to cool in the cell.

While this arrangement provides an improved method of determining conductivity, it suffers from a problem associated with temperature control. As previously discussed, conventional temperature control techniques are often quite bulky and can involve a large refrigerator-like chamber.

Accordingly, the need still exists for a means to provide a constant temperature to this syringe-type test cell.

It is therefore an object of the present invention to provide a constant temperature jacket for such a conductivity test cell.

Another object of the present invention is to provide an improved apparatus for measuring the conductivity of a solid electrolyte.

These and other objects will become apparent from the specification and claims which follow.

SUMMARY OF THE INVENTION

In accordance with the foregoing objectives, the present invention relates to an apparatus for measuring the conductivity of an electrolyte which includes a syringe-type conductivity cell and a constant-temperature jacket in thermal contact with the cell. This jacket allows for heat transfer by conduction and comprises a material having a desired thermal conductivity. Furthermore, the jacket includes means for holding a temperature sensing device, such as a thermocouple; a fluid channel; and a means for holding a syringe-type conductivity cell in thermal contact with the jacket. The apparatus also includes means for introducing a constant-temperature fluid into the fluid channel.

The material employed in producing this jacket is preferably aluminum or copper. Preferably, this jacket has insulation, such as a closed cell foam, wrapped on at least a portion thereof.

In another aspect, the present invention relates to a method which utilizes this jacket for temperature control of a syringe-type conductivity cell.

BRIEF DESCRIPTION OF THE DRAWINGS

FIG. 1 illustrates a syringe-type conductivity cell; and

FIGS. 2a and 2b illustrate one embodiment of a constant-temperature jacket according to the present invention.

DETAILED DESCRIPTION OF THE PREFERRED EMBODIMENTS

The present invention employs a constant temperature jacket which utilizes conductive heat transfer in order to control the temperature within a conductivity cell.

The constant temperature jacket according to the present invention is made from any material which has a desired degree of thermal conductivity. Accordingly, the choice will depend on the degree of temperature control desired for the jacket. Suitable materials include copper, aluminum, silver and gold, with copper and aluminum being preferred.

In the alternative, the jacket can be made from materials selected to provide other properties. For example, the jacket can be made from crystal or lead glass to provide transparency.

The constant temperature jacket can also be wrapped in a layer of suitable insulation, such as closed-cell foam insulation, in order to aid in maintaining a uniform internal temperature.

As illustrated by that embodiment of the invention in FIGS. 2a and 2b, the jacket, 7, includes at least one well, 8, adapted to operationally hold a temperature sensing device, such as a thermocouple. The jacket, 7, includes at least one chamber, 9, sized and adapted to hold the syringe-type conductivity cell in thermal contact with the jacket. As indicated in FIG. 2b, the jacket may contain a plurality of chambers, or wells, adapted to hold syringe type conductivity cells. Seven such chambers, or wells, are indicated in FIG. 2b. Returning to FIG. 2a, the jacket, 7, also contains a fluid channel, 4. The fluid channel has an inlet, 5, for entry of a constant temperautre fluid into the jacket, and an outlet, 6, for fluid exit from the jacket's fluid channel.

Although the present invention is discussed in terms of the syringe-type conductivity cell, any other suitably shaped, i.e., largely longitudinal, conductivity cell, or other device in which temperature control is desired, may effectively be employed with the constant temperature jacket of the present invention.

The constant-temperature jacket includes a fluid channel for circulating a constant-temperature fluid therethrough. This fluid channel preferably has means for connecting the channel with the fluid supply (not shown). Such means can include a hose barb or a quick connection such as a Swage Lok® QC4.

This fluid can be supplied by any art recognized means for providing a constant-temperature fluid such as a constant-temperature bath/circulator, for example, chiller model RTE 110 from NESLAB Instruments, Inc.

The constant temperature jacket, as well as each of the means for holding a temperature measuring device, the conductivity-cell and the fluid channel are each preferably cylindrical in shape, although other shapes can be employed.

In an alternative embodiment, the constant temperature jacket can have a shape of a cylindrical or hollow tube. In this embodiment, the temperature sensing devices as well as the syringe-type conductivity cell can be held in place by suitable means such as an end cap (not shown) for the jacket or thin hollow "sleeves". In such an arrangement, the constant temperature fluid is introduced through the end cap into the jacket where it comes into more immediate contact with the conductivity cell(s) therein. Because conduction occurs more directly between the fluid and the cell in this case, the material of construction for the jacket is not as critical.

Each of the embodiments of the present invention employs conduction in order to transfer heat into or out of the conductivity cell. Conduction is a more efficient and effective process than the more traditionally employed convection, in which hot or cool air currents are used to control the temperature of a sample. Thus, a shorter equilibration time is needed to achieve a desired steady-state condition.

Because of this superior temperature control, the measurement of conductivity can be made relatively quickly at a wide range of reproducible temperatures such as for example, from −20° or −30° C. to +85° C. or even higher. Thus, the present invention simplifies a number of operations, for example, the production of an Arrhenius plot for a particular material.

While the invention has been described in terms of various preferred embodiments, the artisan will appreciate the various modifications, substitutions, omissions, and changes that may be made without departing from the spirit thereof.

I claim:

1. Apparatus for determining the conductivity of an electrolyte comprising:
   (a) at least one conductivity cell comprising a generally longitudinal, cylindrical wall and two electrode rods, one electrode rod extending into each end of the cell, wherein the two electrodes define a volume for testing the conductivity of an electrolyte introduced into the volume; and
   (b) a constant temperature jacket for controlling the temperature of an electrolyte in said cell, said jacket comprising:
      (i) at least one longitudinal chamber for holding a conductivity cell according to (a);
      (ii) means for holding a temperature sensing device; and
      (iii) a fluid channel, said channel having an inlet for fluid entry into said channel and an outlet for fluid exit from said channel wherein said channel is in fluid communication with a source of constant temperature fluid and further wherein at least one of said longitudinal chambers has a conductivity cell according to (a) located therein.

2. The apparatus according to claim 1 wherein the constant temperature jacket is made from a material having a desired degree of thermal conductivity.

3. The apparatus according to claim 2 wherein the material comprises aluminum or copper.

4. The apparatus according to claim 2 further comprising insulation wrapped on at least a portion of the constant-temperature jacket.

5. The apparatus according to claim 1 wherein the temperature sensing device is a thermocouple.

6. The apparatus according to claim 1 wherein the constant temperature jacket has a cylindrical shape having an end cap on each end thereof; wherein the end cap includes the means for holding a temperature sensing device and a means for holding a conductivity cell in the longitudinal chamber.

* * * * *